(12) United States Patent
Geipel (10) Patent No.: US 8,943,894 B2
(45) Date of Patent: Feb. 3, 2015

(54) MICRO-FLUIDIC DEAD-END CHANNEL STRUCTURE FOR PRESSURE MEASUREMENT WITHIN A FLUID CHANNEL ON THE BASIS OF THE CHANGE OF THE VOLUME OF A TRAPPED GAS BUBBLE

(71) Applicant: Roche Diagnostics International AG, Rotkreuz (CH)

(72) Inventor: Andreas Geipel, Oftringen (CH)

(73) Assignee: Roche Diagnostics International AG, Rotkreuz (CH)

( * ) Notice: Subject to any disclaimer, the term of this patent is extended or adjusted under 35 U.S.C. 154(b) by 202 days.

(21) Appl. No.: 13/757,995

(22) Filed: Feb. 4, 2013

(65) Prior Publication Data
US 2013/0139602 A1    Jun. 6, 2013

Related U.S. Application Data

(62) Division of application No. 12/615,338, filed on Nov. 10, 2009, now Pat. No. 8,394,051.

(30) Foreign Application Priority Data

Nov. 14, 2008  (EP) .................................... 08169210

(51) Int. Cl.
*G01L 11/00*    (2006.01)
*G01L 7/00*    (2006.01)
(Continued)

(52) U.S. Cl.
CPC .  *G01L 7/00* (2013.01); *G01L 11/00* (2013.01); *A61M 5/141* (2013.01); *A61M 5/16854* (2013.01); *G01K 5/28* (2013.01); *A61M 2205/3386* (2013.01)

USPC ........................................................... 73/700

(58) Field of Classification Search
CPC ......................................................... G01L 11/00
USPC ...................................................... 73/701, 747
See application file for complete search history.

(56) References Cited

U.S. PATENT DOCUMENTS

| 3,435,819 | A |   | 4/1969 | Reynolds et al. |
| 3,802,265 | A | * | 4/1974 | Wood .......................... 73/861.47 |

(Continued)

FOREIGN PATENT DOCUMENTS

| DE | 3209721 A1 | 9/1983 |
| EP | 0 619 476 A1 | 9/1993 |

(Continued)

OTHER PUBLICATIONS

European Search Report, Appln. No. EP 12 19 6798, Feb. 20, 2013, 6 pages.

*Primary Examiner* — Hezron E Williams
*Assistant Examiner* — Nathaniel Kolb
(74) *Attorney, Agent, or Firm* — Dinsmore & Shohl LLP (57) ABSTRACT

A device for detecting pressure and/or temperature changes in a fluid-channel and method thereof are disclosed. The device includes a main duct with an inlet and an outlet, a branch ductwork with a first branch end branching off the main duct downwards the inlet and with a second branch end discharging into the main duct upwards the outlet, and at least one dead-end channel with a first end that branches off the branch ductwork and a second closed end. The dead-end channel is adapted to trap a gas bubble within the dead-end channel when the device is primed or filled with a liquid fluid, wherein the gas bubble changes its size or position if a change in pressure or temperature occurs in the device.

13 Claims, 7 Drawing Sheets

(51) Int. Cl.
*A61M 5/14* (2006.01)
*A61M 5/168* (2006.01)
*G01K 5/28* (2006.01)

(56) References Cited

U.S. PATENT DOCUMENTS 4,363,321 A   12/1982   Chittenden
5,741,216 A   4/1998   Hemmingsen et al.
6,575,026 B1 *  6/2003   DeBar et al. .................... 73/202
6,843,121 B1 *  1/2005   DeBar et al. .................... 73/202
2003/0006140 A1  1/2003   Vacca et al.

FOREIGN PATENT DOCUMENTS

EP   1 762 263 A1   3/2007
WO   93/20865       10/1993
WO   01/20271 A1    3/2001
WO   01/72359 A1    10/2001

* cited by examiner

MICRO-FLUIDIC DEAD-END CHANNEL STRUCTURE FOR PRESSURE MEASUREMENT WITHIN A FLUID CHANNEL ON THE BASIS OF THE CHANGE OF THE VOLUME OF A TRAPPED GAS BUBBLE

This patent application is filed under 35 U.S.C. §111(a) as a division of U.S. application Ser. No. 12/615,338, filed Nov. 10, 2009, which claims the benefit of European Patent Application No. EP08169210.5, filed Nov. 14, 2008.

TECHNICAL FIELD

Embodiments of the present invention relate to a device for measuring pressure and/or temperature changes in a liquid fluid flowing through the device comprising a main duct, a branch ductwork and at least one dead-end channel wherein a gas bubble is trapped inside the dead-end channel as well as an ambulatory or administration device for the administration of a liquid drug into a patient's body over an extended time period and a method for measuring a change in pressure and/or temperature within the device.

BACKGROUND

Known in the art are devices which comprise a main duct and a dead-end channel branching off the main duct wherein a gas bubble is trapped in the dead-end channel when the device is being filled with a liquid fluid. It is also known to integrate a gas-permeable membrane (e.g. PTFE) at the open end of the dead-end channel to allow for a partially or entirely filled dead-end channel. These devices can e.g. be used as actuators using the temperature-dependent extension of the gas bubble to start or stop certain activities of a system. Other uses in the range of micro-fluidics are known. However, the installation of such devices into insulin pumps is not known in the art.

Such a simple dead-end channel structure has big disadvantages if used as a pressure sensor in a liquid fluid-path as the gas bubble inside the dead-end channel can leak from the dead-end channel and invade the main duct. This could lead to a failure in the liquid fluid stream through the main duct such as influencing the amount of liquid fluid reaching the end or outlet of the main duct.

SUMMARY

It is against the above background that the embodiments of the invention concern a device for measuring a pressure and/or temperature change in a fluid channel and a method for detecting pressure and/or temperature changes therein.

In one embodiment, a device for detecting pressure and/or temperature changes in a fluid channel is disclosed. The device comprises a main duct with an inlet and an outlet, a branch ductwork with a first branch end branching off the main duct downwards the inlet and with a second branch end discharging into the main duct upwards the outlet, and at least one dead-end channel with a first end that branches off the branch ductwork and a second closed end. The at least one dead-end channel traps a gas bubble within the dead-end channel when the device is primed or filled with a liquid fluid, wherein the gas bubble changes its size or position if a change in pressure or temperature occurs in the device, and wherein the branch ductwork prevents an expanding gas bubble from escaping into the main duct.

In another embodiment, a method for detecting pressure and/or temperature changes in a fluid channel is disclosed. The method comprises feeding a liquid fluid into a main duct through an inlet; branching off the main duct downwards of the inlet a branch ductwork such that the fluid is led through the main duct and the branch ductwork; and branching off the branch ductwork a dead-end channel such that the liquid fluid passing by is hemming air in the dead-end channel, whereby a gas bubble is built in the dead-end channel, and wherein the size and/or the position of the gas bubble varies with different pressure or temperature values inside the fluid channel and the branch ductwork prevents an expanding gas bubble from escaping into the main duct.

These and other advantages and features of the invention disclosed herein will be made more apparent from the description, drawings and claims that follow.

BRIEF DESCRIPTION OF THE DRAWINGS

A detailed description of embodiments of the invention will be made with reference to the accompanying drawings, wherein like numerals designate corresponding parts in a several figures, wherein.

LIST OF REFERENCE SIGNS 1 main duct
2 branch ductwork
3 dead-end channel
4 gas bubble, gas
5 hydrophilic layer
6 hydrophobic layer 7 meniscus
8 sensor
9 sensor
10 inlet
11 outlet
12 branching-off end, first end
13 discharging end, second end
14 open end
15 closed end
16 liquid fluid
17 light source
18 detector
19 point of incidence
20 detector
21 flow-barrier
β angle of incidence

DETAILED DESCRIPTION

In one embodiment, a device for measuring a pressure change in a liquid fluid is disclosed. The device comprises a main duct with an inlet and an outlet, at least one branch ductwork with a first branch end, branching off the main duct downwards the inlet and with a second branch end discharging into the main duct upwards the outlet. The device further comprises at least one dead-end channel with a first end branching off the branch ductwork and a second closed end. Whenever the device is primed or filled with a liquid fluid a gas bubble is built within the dead-end channel, wherein the size or the position of the gas bubble changes if a change in pressure and/or temperature occurs in the liquid fluid.

The size of the bubble may change if the temperature of the liquid fluid inside or flowing through the device changes, that means, the size of the bubble may increase if the temperature is rising, if the temperature falls the size of the bubble may decrease. If the pressure within the device is rising the gas bubble may be compressed or decreased and consequently a falling pressure inside the system will cause the gas bubble to expand or increase. In other words rising temperature and falling pressure lead to an expanding gas bubble, falling temperatures and rising pressure lead to a compressed gas bubble. It is obvious that in the occurrence of an occlusion or leak upstream or downstream in the device, the pressure inside the device will rise or fall accordingly.

Instead of one dead-end channel the device can comprise two or more dead-end channels, both or all branching off the same branch ductwork. If, however, the device comprises more than one branch ductwork, each branch ductwork may comprise one or more dead-end channels. If the device comprises more than one dead-end channel one of them could also branch off the main duct while the other or the others branch off the one or more branch ductwork.

The dead-end channel(s) can branch off the respective main duct or branch ductwork perpendicular or at any desired angle, from 1° to 179°. Preferably, the branch ductwork branches off at an angle between about 30° and about 150°, and more preferably at an angle of approximately 90°. The dead-end channel can also branch off perpendicularly from the respective duct and be bent in any direction behind the branching off-point. For example, the dead-end channel may run parallel to the duct it is branched off or point in any direction desired that is allowed by the construction of the device. The length of the dead-end channel can be chosen according to requirements; the same applies to the bending point of the dead-end channel.

The branch ductwork or a part of the branch ductwork may have a cross sectional area smaller than the cross sectional area of the main duct, and the cross sectional area of the dead-end channel can be smaller, equal or greater than the cross sectional area of the duct it is branching off. At least the branch ductwork can be a tapered channel, e.g. the walls of the branch ductwork do not have to run parallel to each other but the distance between these walls can change so that regions of different channel cross sectional areas are formed inside the branch ductwork. The dead-end channels can also comprise regions of different cross sectional area or the closed end of the dead-end channel or an intermediate part thereof can be formed as a balloon or any other suited kind of cavity.

The branch ductwork is designed such that an expanding gas bubble does not escape from the branch ductwork into the main duct. In preferred embodiments, the expanding bubble inside the dead-end channel displaces the flow-barrier in form of a meniscus (liquid/air bubble border) from the dead-end channel in a generally straight line into the branch ductwork, which, in this case, preferably has the same cross section as the dead-end channel. Interferential forces prevent the gas bubble from entering the main duct or passing the discharging point. Therefore, it is to be appreciated that the design of the branch ductwork ensures that (for a given operational pressure and temperature range for which the device is designed) the gas bubble stays in the dead-end channel even in the case of temperature changes which result in an expansion of the gas bubble and/or in case of a negative pressure in the fluid-channel which also results in an expansion of the gas bubble. Both situations are likely to occur in the field of (insulin) infusion or administration of a liquid drug into a patient's body over an extended time period.

The inside of the device or parts thereof can comprise a hydrophilic layer and/or a hydrophobic layer in one embodiment. Preferably the dead-end channel or parts thereof are on the inside covered with a hydrophobic layer while the branch ductwork or parts of the branch ductwork comprise a hydrophilic layer covering the inside thereof. If the branch ductwork comprises regions of different cross sectional areas it is advantageous if at least the regions with the smaller cross sectional area are covered with a hydrophilic layer on their respective inside.

Both the branch ductwork and the main duct built a flow-barrier at the discharging point where the branch ductwork discharges into the main duct. The hold will continue until both the branch ductwork and the main ductwork are filled with the liquid fluid up to the discharging point. That means, as the fluid passing through the smaller branch ductwork reaches the discharging point prior to the fluid running through the main duct the fluid in the branch ductwork will stop at the discharging point due to the appearance of interfacial energy.

As the fluid-system always aims to minimize the interfacial energy the meniscus comes, for example, to a hold where a duct with a small cross sectional area opens out into a duct with a greater cross sectional area as otherwise the interface between fluid and gas would have to be enlarged immensely. Interfacial tension is a measure for the amount of energy necessary to enlarge the interface and leads to a curvature of the meniscus in small ducts resulting in a capillary decrease in pressure cross the interface. This phenomenon is especially strong developed in a device where a duct with a small cross sectional area with a hydrophilic layer on its inside opens out into a duct with a large cross sectional area with a hydrophobic layer on its inside.

To allow for detecting and/or measuring a change in temperature and/or pressure inside the device, the device can comprise detecting assemblies, such as a sensor in one embodiment. Such assemblies should be able to detect continuously a change in the size of the gas bubble and thus a change in position of a meniscus, which forms the border between the liquid fluid and the gas. As the length of the gas bubble and thus the position of the meniscus depend on the pressure or temperature inside the device, the change in the size of the bubble is an indication for a change of temperature and/or pressure inside the device, allowing for an indirect measurement for the temperature and/or the pressure inside the device. This means that the sensor in one embodiment is placed inside the dead-end channel in a section where the meniscus lies and moves during normal operating conditions to allow for detecting a change in temperature and/or pressure of the liquid fluid. This continuous method supplies the information that a given pressure or temperature is maintained within given borders. If a discrepancy of the temperature and/or pressure is detected this information could be supplied to an alarm assembly which could inform the user acoustically, visually or for example by vibration.

A threshold detection method detecting the position of the meniscus may be used in one embodiment if a pressure and/or temperature threshold detection is sufficient. In the case that a overstepping of the threshold value is detected an acoustic, visual or tactile alarm can be triggered to warn the user and/or the alarm signal can be supplied to a control unit which can cut off a pump delivering the fluid to the device or can open a fluidic bypass to allow the fluid to return to a reservoir. This method could be sufficient for detecting a blocked occlusion line, a preferred field of application for the embodiments of the invention.

Against the threshold measuring method, the continuous measuring of the position of the meniscus allows to adaptively modify the threshold value and to employ more sophisticated filtering and/or evaluation algorithms.

An additional or alternative sensor in another embodiment can be positioned around the dead-end channel in the form of isolated electrodes which control the position of the meniscus with a capacitive detection. The capacitive detection allows for a continuous or clocked detection. Typically the measurement concerns a change in the capacitance, impedance or admittance. The electrode arrangement can comprise two planar electrodes positioned side by side, finger-electrodes above the channel or electrodes on opposed sides of the channel.

Another method embodiment is the method of measuring the different resistance of the fluid (like insulin) and the gas bubble, the method being described in detail in EP1762263A1. The measurement voltage is normally a low potential voltage between about 0.5V to about 15V, preferably about 1.5V to about 5V, even more preferred between about 1.5V to about 3V, wherein the voltage can be direct voltage or an AC voltage between about 10 Hz to about 100 kHz. In one preferred embodiment, the measuring frequency would be about 1 kHz.

If the position of the meniscus is controlled optically the light source might be a LED and the detector e.g. a photodiode or diode-array. The light might be supplied to the measuring position via fibre optics or another optical coupling structure known in the art and optical effects used for detection can be absorption, reflection, refraction, diffraction, interference, dispersion, evanescent field, and so on.

Alternative methods to control the position of the meniscus can be the change in colour against a change of pressure, ultrasonic bubble control, heat conduction or heat radiation.

In the case of the continuous measurement the detector collects a large area which covers at least the dead-end channel or the dead-end channel and a part of the branch ductwork, which in this case preferably has the same cross sectional area as the dead-end channel, but different cross sectional areas also are within the scope of the invention. The position of the meniscus correlates preferably proportional or hyperbolic with resistance (galvanic interfacing), with capacity (capacitive interfacing) or with the picture projection (optical interfacing). The threshold to trigger an alarm will be determined by the processing of the sensor signal e.g. by using an electronic control of the hardware through or by programming a microcontroller which is part of the software. In the case that the overstepping of the threshold value is detected an acoustic, visual or tactile alarm can be triggered to warn the user and/or the alarm signal can be supplied to a control unit which can cut off a pump delivering the fluid to the device or can open a fluidic bypass to allow the fluid to return to a reservoir. A continuous measurement according to the invention includes a quasi-continuous measurement with e.g. numerous of discrete electrodes.

A device according to the embodiments of the invention can be made of plastic material, preferably of slightly hydrophilic thermoplastic, such as PMMA, polyamide, polycarbonate, PSU, ABS, PBT, PEEK, COC and LCP. Alternatively materials like glass, silicon or metal can be used. Combinations of these materials are also possible.

The ducts may have a round, square, rectangular or polygonal cross sectional area, the preferred form is round. The main duct, the dead-end channel and parts of the branch ductwork of the device can for example have a cross sectional dimension of about 50 to about 1000 µm while section of the ducts building constrictions can have a cross sectional dimension between about 10 to about 250 µm. If a square or rectangular form is chosen the hydraulic cross sectional dimension $D_{hydr.}=4A/U=(4 \times b \times h)/(2b+2h)$ is used, wherein b stands for the width of the duct and h represents the height of the duct.

Generally, the material and the dimensions of the device are preferably designed such that the behaviour of the liquid and the gas is largely determined by the pressure in the device and the interferential and/or borderline effects, while gravity forces are negligible. That is pressure, surface tension and/or capillary effects prevail over gravimetric and/or buoyancy effects.

A device according to the embodiments of the invention may be built by the implementation of injection molding, injection coining, hot stamping, the device can be formed by cutting techniques such as milling or thrilling, or it can be manufactured by micro-technical methods such as chemical etching or wet etching, dry etching (ion beam, plasma, and laser), laser ablation or electrical discharge machining.

Parts of the device can be assembled or can be closed using welding techniques such as ultrasound, heat or laser, glues like UV-glue, for example, thermo-bonding or plasma-bonding or several multilayer methods.

The above mentioned electrodes or parts of the sensors can be integrated in the device structure by MID, shrink-wrapping (foil with conductors printed on), foil back injection moulding (foil with conductors printed on) or hybrid integration of printed boards (flexible or rigid).

Examples of methods to modify the inner surface of the ducts are in order to establish a hydrophilic layer: coatings, such as hydrophilic functionalising self-assembling monolayer; monomolecular polymeric layers; silanization; fire-pyrolysis; plasma-activation. The preferred method in one embodiment is dispensing; and a hydrophobic layer: micro-structuring; coatings, such as such as hydrophobic functionalising self-assembling, monolayer, monomolecular polymeric layers, parylene, PTFE, fluoropolymer.

Embodiments of the invention also concern an ambulatory or administration device for the administration of a liquid drug into a patient's body over an extended time period. The device comprises a drug reservoir, a pump system operatively coupled to the reservoir, an infusion cannula to be placed in the patient's subcutaneous tissue, and a device for detecting a pressure and/or temperature change as described above. The ambulatory or administration device can further comprise an alarming unit adapted to provide an alarm in case of at least one predefined pressure condition, wherein at least one predefined pressure condition is the exceeding of a given maximum threshold or the falling below a given minimum threshold of the fluid pressure. The alarm can be a tactile alarm, such as a vibration of the ambulatory or administration device or a part of it, a visible advice, such as a blinking LED of preferably red colour or any suitable audible alarm, such as a continuous or non-continuous tone.

The reservoir can be part of the housing of the ambulatory or administration device and the device itself can be a disposable injector. If, however, the device is a reusable device, the reservoir can be an integrated part of the device which can be refilled or it can be a replaceable ampoule.

Furthermore, the embodiments of the invention comprise a method for detecting pressure chances in a fluid channel, wherein a liquid fluid is fed into a main duct through an inlet, downwards said inlet a branch ductwork is branching off the main duct and the liquid fluid is lead through said main duct and said branch ductwork, a dead-end channel is branching off said branch ductwork and the fluid passing by is hemming air in said dead-end channel whereby a gas bubble is built in said dead-end channel, characterised in that the size of the gas bubble and/or the position of a border separating said gas bubble and said liquid fluid varies with different pressure and/or temperature values inside the ducts.

The various embodiments of the invention will now be described by means of several specific illustrative embodiments depicted by the figures. The specifications regarding these illustrative embodiments provided hereafter are merely thought to explain in greater detail the advantages of the invention without limiting the content of the invention in any way.

Figure 1:
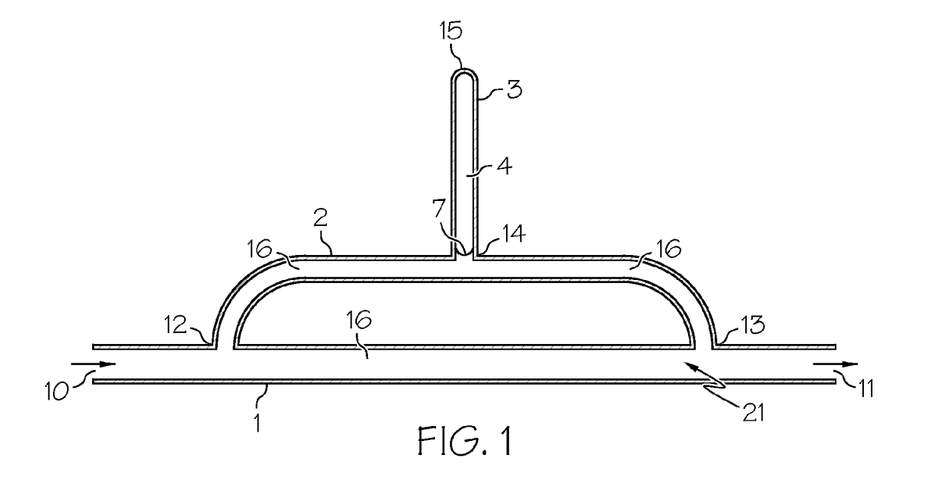
FIG. 1 depicts a device according to an embodiment of the invention with a main duct, a branch ductwork and a dead-end duct.

FIG. 1 shows a device according to an embodiment of the invention with a main duct 1, a branch ductwork 2 and one dead-end channel 3, wherein the main duct comprises an inlet 10 and an outlet 11. The branch ductwork 2 is branching off the main duct 1 at a first end 12 and discharging into the main duct 1 at a second end 13. The dead-end channel 3 is branching off the branch ductwork at its open end 14. As can be seen, the cross sectional area of the branch ductwork 2 is smaller than the cross sectional area of the main duct 1.

When a fluid is entering the device and reaches the point where the first end 12 branches off the main duct 1 the flow of the fluid will be divided into two part-flows. The first or main part-flow will continue its way through the main duct 1, while a smaller part-flow will enter the branch ductwork 2. On its way through the branch ductwork 2 the fluid will pass by the open end 14 of the dead-end channel 3, which in the shown example comprises a larger cross sectional area than the branch ductwork 2. In the shown example the dead-end channel 3 branches off the branch ductwork 2 in the middle thereof. This position is only meant as an example as basically the dead-end channel 3 can branch off the branch ductwork 2 at any suitable position.

When flowing by the open end 14 the liquid fluid will trap air or gas separated from the liquid by meniscus 7 in the dead-end channel 3. The main flow through main duct 1 and the part-flow through branch ductwork 2 reunite at the point where the second end 13 of the branch ductwork 2 discharges into the main duct 1. The main stream flowing through the main brunch 1 may reach the discharging point prior to the part stream flowing through the branch ductwork 2. Due to interfacial forces a flow-barrier 21 will be built at the discharging end (e.g., second end 13) of either branch. The main stream through the main duct 1 will come to a stop at the discharging point of the second end 13 and continue its flow as soon as the branch ductwork 2 is filled with fluid up to the discharging point of the second end 13.

Figure 2:
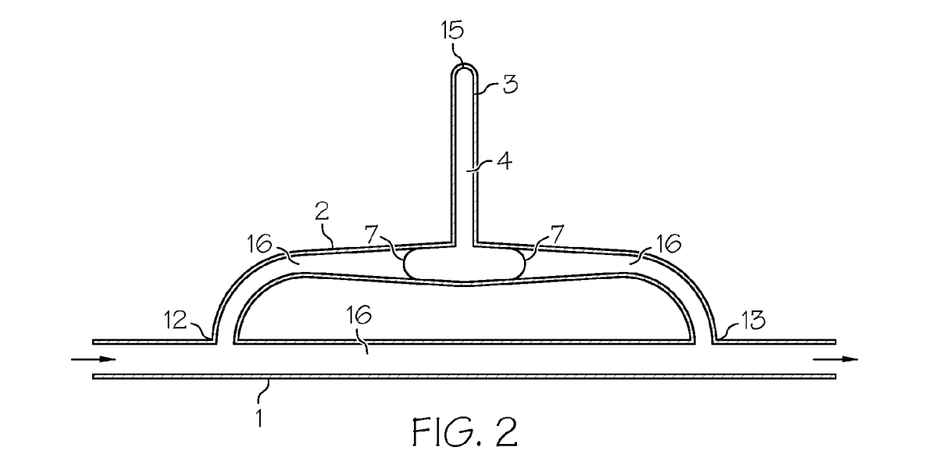
FIG. 2 depicts the device of FIG. 1 with a tapered branch ductwork.

FIG. 2 basically shows the device of FIG. 1 with a branch ductwork 2 comprising a tapered channel. The example of the tapered channel shown in FIG. 2 is only exemplary and is not meant to limit the geometric design. Basically the tapered channel can have any form suitable for a specific application.

Any change of pressure or temperature inside the device will have an impact on the trapped gas bubble 4. In the example shown in FIG. 2 the pressure inside the device is decreased in comparison to the filling situation. Due to this difference in pressures the gas bubble 4 expands into the branch ductwork. It is to be appreciated that one of the advantages of the invention is that despite the expanded gas bubble 4 the flow of the fluid through the main duct 1 is in no way affected.

The device in one embodiment can e.g. be implemented in an injection device between the reservoir and the dosing unit. In such an embodiment the occurrence of a decrease in pressure can indicate to the user, or a not shown control unit, that the reservoir is empty or that a leak or an occlusion exists somewhere downstream of the device.

Figure 3:
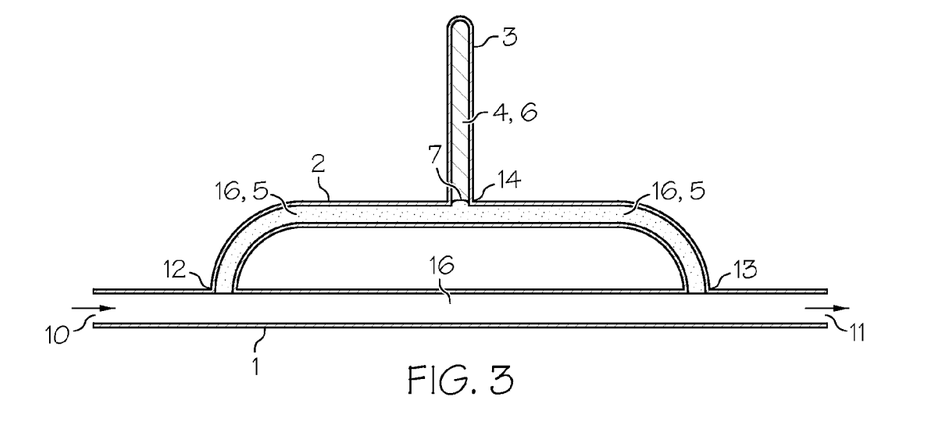
FIG. 3 depicts the device of FIG. 1 with the inside of the branch ductwork covered with a hydrophilic layer and the inside of the dead-end channel covered with a hydrophobic layer.

FIG. 3 shows the device of FIG. 1 wherein the branch ductwork 2 and the dead-end channel 3 are covered on their inside with a layer. In one embodiment the branch ductwork 2 comprises on its inner surface a hydrophilic layer 5 which allows for a better flow of the liquid fluid 16 through the branch ductwork 2, while the dead-end channel 3 comprises on its inner surface a hydrophobic layer 6 which avoids the wetting of the dead-end channel 3. Any hydrophilic or hydrophobic material can be used as long as it can be applied on the inner surface. One method of applying the layer can for example be the method of evaporation deposition.

Figure 4:
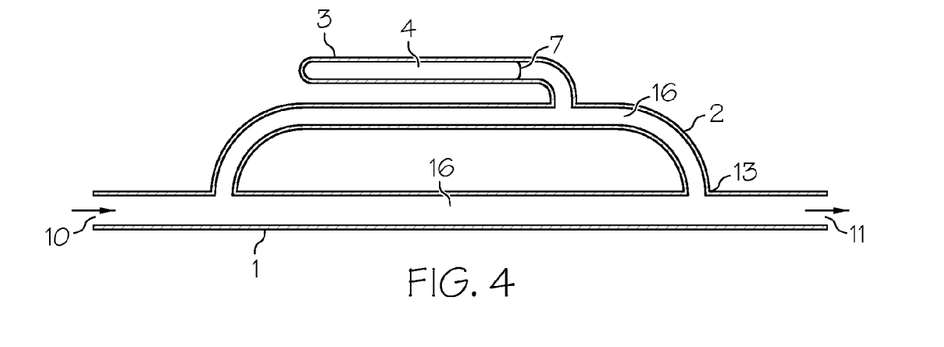
FIG. 4 depicts the device of FIG. 1 with the dead-end duct running parallel to the branch ductwork.
Figure 5:
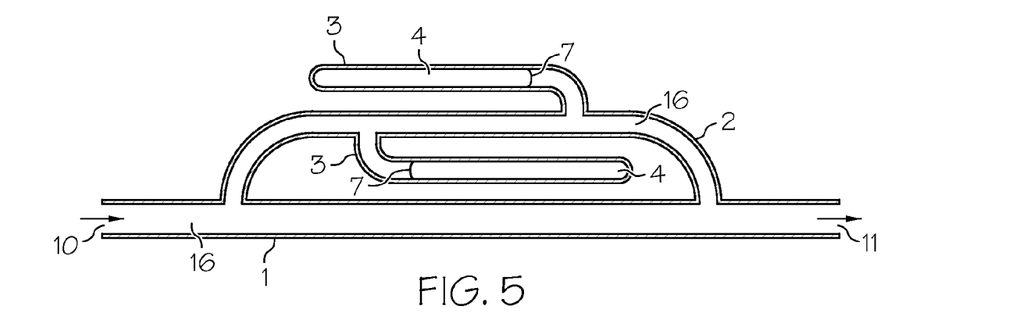
FIG. 5 depicts the device of FIG. 4 comprising two dead-end channels.
Figure 6:
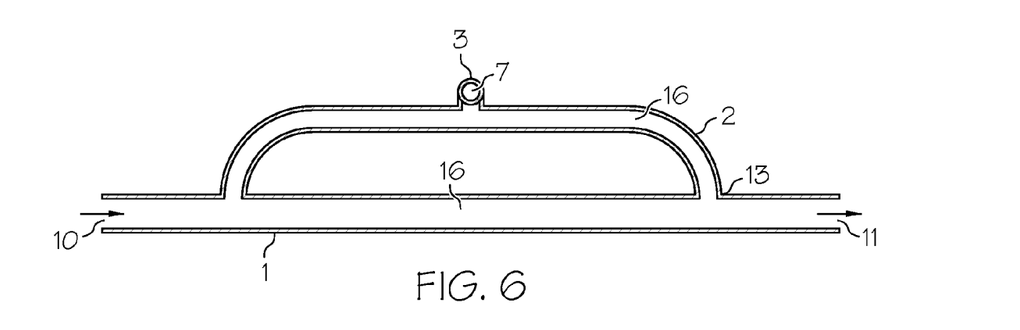
FIG. 6 depicts the device of FIG. 4 with the dead-end channel transverse to the branch ductwork.

FIG. 4 shows an embodiment that is basically the device of FIG. 1 with a bent dead-end channel 3 running parallel to a part of the branch ductwork 2 and to the main duct 1. FIG. 5 shows an another embodiment of the device of FIG. 4 comprising two dead-end channels 3. Both dead-end channels 3 branch off the same branch ductwork 2 and both of dead-end channels 3 each has a sealed in gas bubble 4. A meniscus 7 is built between each of the gas bubbles 4 and the liquid inside the device. FIG. 6 shows still another embodiment of the device of FIG. 4 with a bent dead-end channel 3 running cross to the branch ductwork 2. In the embodiment of FIG. 6 the dead-end channel 3 branches off the branch ductwork 2 in a first direction and is bent in a crosswise direction just behind the branching off point. The dead-end channel 3 could as well branch off the branch ductwork 2 directly from the side. Basically, the dead-end channel 3 might branch off the branch ductwork 2 at any point of its circumference or length.

Figure 7:
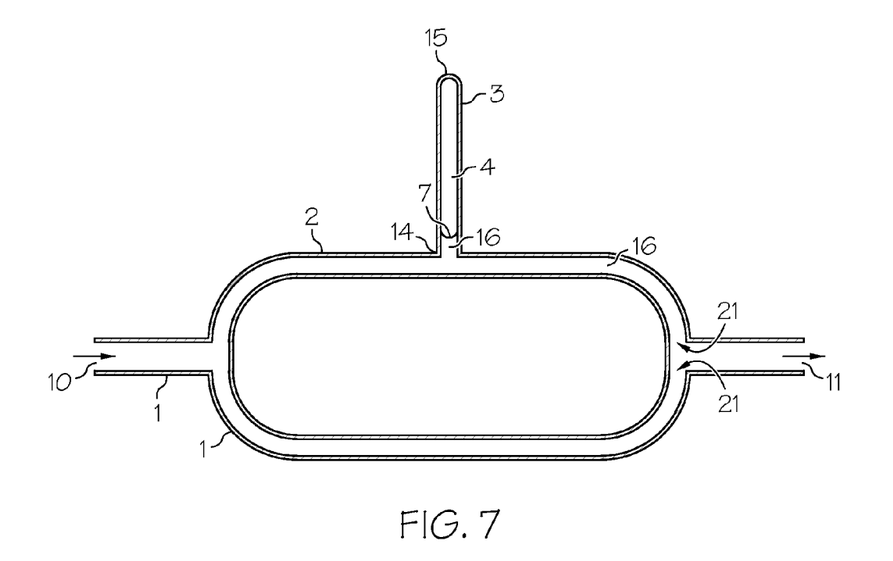
FIG. 7 depicts a device according to another embodiment of the invention with a flow-barrier on both sides of the discharging point.

FIG. 7 shows yet another embodiment of the invention. The device of FIG. 7 comprises a main duct 1 splitting of in two channels of equal cross sectional area wherein one of the channels continues the main duct 1 while the other channel forms the branch ductwork 2 from which the dead-end channel 3 is branching off. The two channels each have the same cross sectional area which is smaller than the cross sectional area of the main duct 1 before the split. Downstream the branching off point of the open end 14 of dead-end channel 3 the two channels discharge in the main duct 1 comprising the same cross sectional area as at the inlet 10. Each of the two channels builds a flow-barrier 21 at its respective downstream end.

Figure 8:
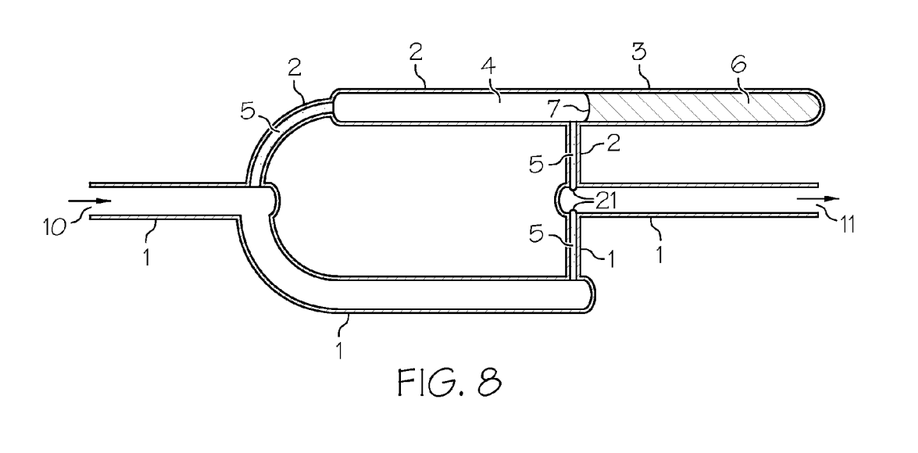
FIG. 8 depicts a device according to still another embodiment of the invention with a hydrophilic layer on the inside and regions with a small cross sectional area.

FIG. 8 shows another embodiment of the device of the invention. The main duct 1 comprises a first section with a first cross sectional area and a second section with a second cross sectional area, wherein the second cross sectional area is substantially smaller than the first cross sectional area. The branch ductwork 2 comprises a first section with a first cross sectional area, a second section with a second cross sectional area and a third section with a third cross sectional area, wherein the first and the third cross sectional area are small in comparison to the second cross sectional area. From the second section of the branch ductwork 2 a dead-end channel 3 branches off with a cross sectional area equal to the cross sectional area of the second section of the branch ductwork 2. The sections of the main duct 1 and the branch ductwork 2 with the small cross sectional area are covered with a hydrophilic layer 5 on their inside, the dead-end channel 3 has a hydrophobic layer 6 on its inside. These modifications of the inner surfaces are advantageous for a controlled gas bubble handling but are not essential for the operation of the embodiment. This embodiment allows for a controlled displacement of the meniscus 7 in the occurrence of a rise or fall in pressure. It provides a partial isolation of the gas bubble 4 from the main duct 1 due to small connecting channels of the main duct 1 and the branch ductwork 2 and for two flow barriers at the point where the main duct 1 and the branch ductwork 2 are brought together.

Figure 9:
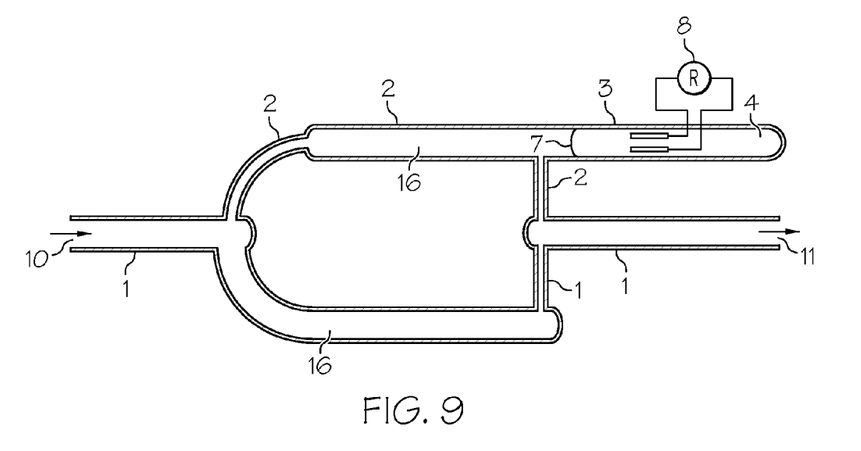
FIG. 9 depicts the device of FIG. 8 with a sensor for threshold detection.

FIG. 9 shows another embodiment of the device of FIG. 8 comprising additionally a sensor 8 placed inside the dead-end channel 3 and thus inside the gas bubble 4. The sensor 8 can detect changes of the pressure inside the gas bubble 4 which can occur if the pressure in the device is rising or falling or if the temperature changes. A rise in pressure inside the device or a descent in temperature will compress the gas bubble 4 while a fall in pressure inside the device or a built-up of temperature will allow the gas bubble 4 to expand. Both lead to a displacement of the meniscus 7 inside or outside the dead-end channel 3. Preferably the sensor 8 detects when the pressure inside the gas bubble exceeds a given threshold. The measured data can be supplied to a not shown control unit which converts the signals received from the sensor. To supply the data to a control unit at least one led of the sensor 8 must be lead through the wall of the dead-end channel 3. This lead can be melted in the wall of the dead-end channel 3 during production or a hole can be drilled through the wall after production and the lead-hole is sealed after implementation of the sensor 8 by clue or a special sealing agent.

Figure 10:
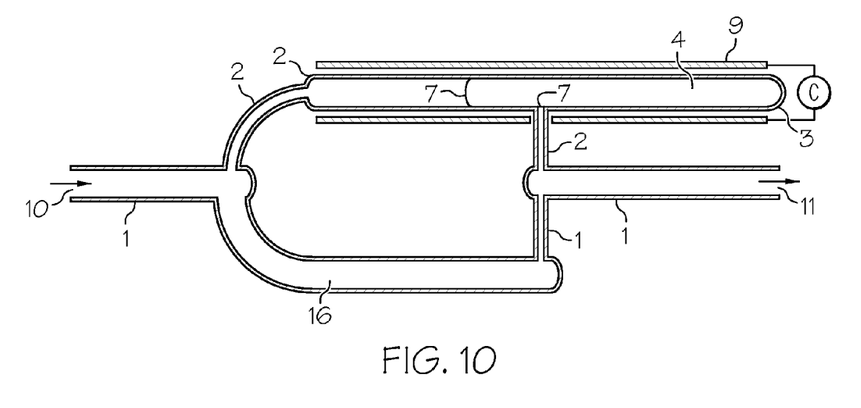
FIG. 10 depicts the device of FIG. 8 with a sensor for capacitive detection.

FIG. 10 shows an embodiment that is similar to the device depicted in FIGS. 8 and 9 with a sensor positioned on the outside of the dead-end channel 3. The sensor 9 in the embodiment of FIG. 10 is built up by isolated electrodes which are fixed to the outside of the dead-end channel 3 and the outside of the second section of the branch ductwork 2 having the same cross sectional area as the dead-end channel 3. As liquid fluid 16 and gas bubble 4 have a different dielectric coefficient it is possible by this capacitive detection to detect the exact position and any movement of the meniscus 7. A movement of the meniscus 7 indicates a change in temperature or pressure, the direction the meniscus 7 is moving indicates whether the pressure in the system is rising or falling or whether the temperature is decreasing or increasing. The capacitive detection allows for a continuous or clocked detection. This measuring method allows for detecting even very small changes in pressure and/or temperature and is easy to apply as the entire sensor 9 is positioned outside the device.

FIG. 10 also shows that the meniscus 7 is displaced along a straight line and is not divided when passing a duct branch, thus allowing the embodiment to be employed for measuring both overpressure and low-pressure. This also holds true for the embodiments according to FIG. 8 and FIG. 9.

Figure 11A:
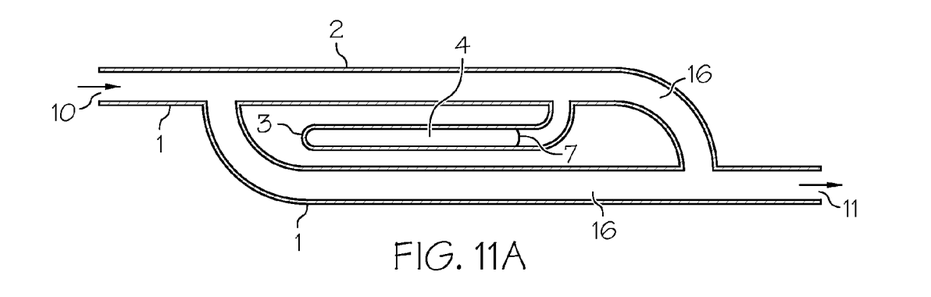
FIG. 11a depicts a device according to yet another embodiment of the invention showing a first offset inlet and outlet embodiment.
Figure 11B:
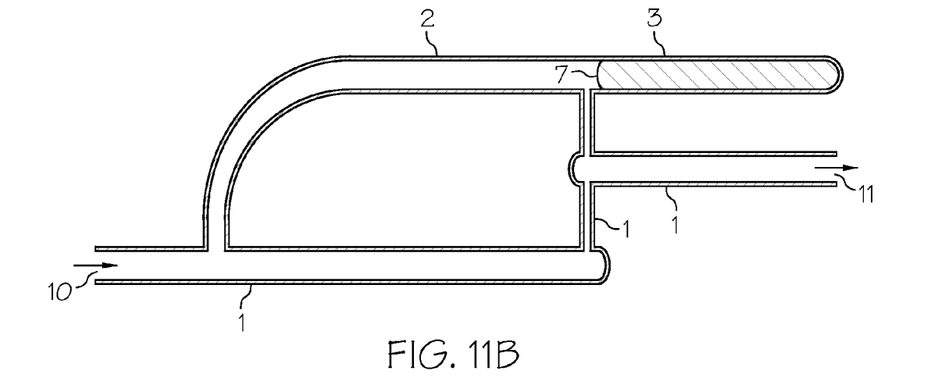
FIG. 11b depicts a device according to still yet another embodiment of the invention showing a second offset inlet and outlet embodiment.

FIG. 11a shows another embodiment of the device of the invention with an outlet 11 of the main duct 1 which is offset in comparison to the inlet of the main duct 1. In this example the dead-end channel 3 is positioned between the main duct 1 and the branch ductwork 2. FIG. 11b shows yet another advantageous embodiment with an offset between outlet 11 and the inlet 10 of the main duct 1.

Figure 12A:
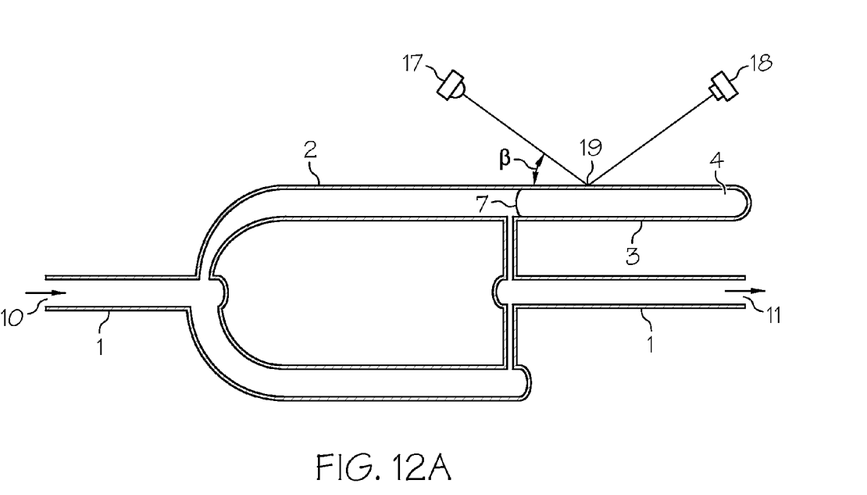
FIG. 12a depicts the device of FIG. 8 with one optical sensor.

FIG. 12a depicts another embodiment of the device of FIG. 8 comprising an optical sensor comprising a light source 17 and a corresponding detector 18. The light source 17 can be a LED diode or a laser diode, for example. The angel of light incidence β may vary between 0° and 90°. Optical effects such as reflection, refraction, absorption or dispersion may be employed to detect if the dead-end channel 3 is filled with liquid fluid or gas at the point of beam incidence 19. In an especially preferred arrangement, the angle of incidence β is chosen such that total reflection occurs if the gas bubble 4 stretches across a point of incidence 19. Accordingly, the point of incidence 19 defines a threshold pressure which passing above or falling below can be detected.

Figure 12B:
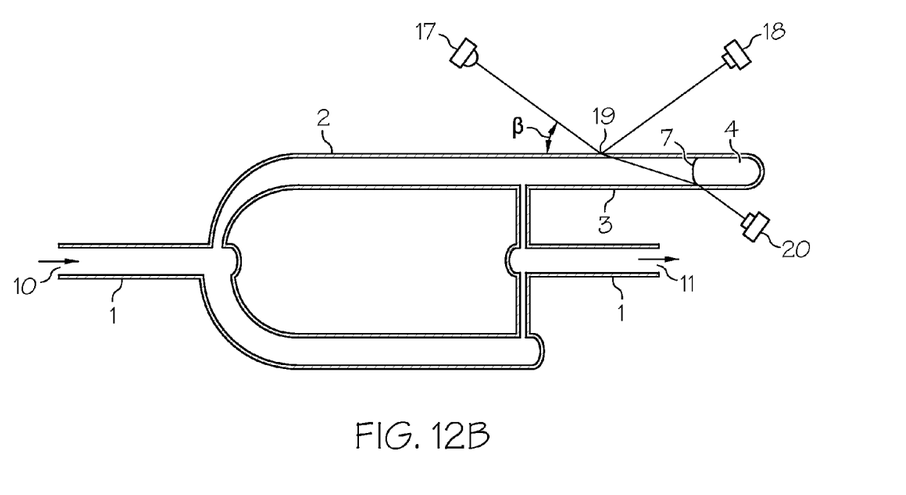
FIG. 12b depicts the device of FIG. 8 with two optical sensors.

In the embodiment shown in FIG. 12b, two detectors 18, 20 are provided for safety reasons. If the gas bubble 4 expands and stretches across the point of incidence 19 in the direction of the branch ductwork 2 total reflection occurs like in the embodiment shown in FIG. 12a. In the case that the gas bubble 4 does not stretch across the point of incidence 19, i.e., the dead-end channel 3 is filled with liquid fluid at the point of incidence 19 the light beam is refracted and passes the dead-end channel 3. In this case, the light beam will hit detector 20. If the light beam fails to hit either detector 18 or detector 20, the device, and in particular the light source, is defective, dirty or the like.

The above described device method allows to detect absolute pressure values between about 0.3 and about 7 bar in one embodiment, and preferably between about 0.5 and about 5 bar in another embodiment.

Having described the disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure. As such, the embodiments described above are purely illustrative and not meant to limit the scope of the invention.

What is claimed is:

1. A method for detecting a change in pressure or temperature in a fluid channel comprising:
   feeding a liquid fluid into a main duct through an inlet, wherein:
      a branch ductwork branches off the main duct downwards of the inlet such that the liquid fluid is led through the main duct and the branch ductwork, and
      at least one dead-end channel branches off the branch ductwork such that the liquid fluid passing by hems in air in the at least one dead-end channel whereby a gas bubble is situated in the at least one dead-end channel; and detecting a change in size or position of the gas bubble, wherein the size or position of the gas bubble changes if a change in pressure or temperature occurs inside the fluid channel, and wherein the branch ductwork prevents an expanding gas bubble from escaping into the main duct.

2. The method of claim 1, wherein the size of the gas bubble increases when the temperature inside the fluid channel rises, and wherein the size of the gas bubble decreases when the temperature inside the fluid channel decreases.

3. The method of claim 1, wherein the size of the gas bubble decreases when the pressure inside the fluid channel increases, and wherein the size of the gas bubble increases when the pressure inside the fluid channel decreases.

4. The method of claim 1, wherein the change in pressure or temperature inside the fluid channel is detected with a means to detect a change of the size or position of the gas bubble.

5. The method of claim 4, wherein the means to detect a change of the size or position of the gas bubble is a sensor.

6. The method of claim 5, wherein the sensor is positioned inside of the dead-end channel.

7. The method of claim 5, wherein the sensor is positioned around the dead-end channel.

8. The method of claim 1, wherein the change in size or position of the gas bubble is detected in a continuous or clocked mode.

9. The method of claim 1, wherein an alarm is triggered in case of at least one predefined pressure condition.

10. The method of claim 9, wherein the at least one predefined pressure condition is exceeding a given maximum threshold or falling below a given minimum threshold of fluid pressure.

11. The method of claim 1, wherein two dead-end channels branch off of the branch ductwork.

12. The method of claim 1, wherein an absolute pressure value of from about 0.3 to about 7 bar is detectable.

13. A method for detecting a change in pressure or temperature in a fluid channel comprising:
feeding a liquid fluid into a main duct through an inlet, wherein:
a branch ductwork branches off the main duct downwards of the inlet such that the liquid fluid is divided into a two part-flow comprising a first part flow and a second part flow, wherein the first part flow flows through the main duct and the second part flow flows through the branch ductwork, and
at least one dead-end channel branches off the branch ductwork such that the second part flow passing by hems in air in the at least one dead-end channel whereby a gas bubble is situated in the at least one dead-end channel; and
detecting a change in size or position of the gas bubble, wherein the size or position of the gas bubble changes if a change in pressure or temperature occurs inside the fluid channel, and wherein the branch ductwork prevents an expanding gas bubble from escaping into the main duct.

* * * * *

UNITED STATES PATENT AND TRADEMARK OFFICE
CERTIFICATE OF CORRECTION

PATENT NO. : 8,943,894 B2
APPLICATION NO. : 13/757995
DATED : February 3, 2015
INVENTOR(S) : Andreas Geipel It is certified that error appears in the above-identified patent and that said Letters Patent is hereby corrected as shown below:

In the Specification

Col. 6, Line 65,
 "structuring; coatings, such as such as hydrophobic function-" should read
 --structuring; coatings, such as hydrophobic function- --;

Col. 7, Line 24,
 "method for detecting pressure chances in a fluid channel," should read
 --method for detecting pressure changes in a fluid channel,--;

Col. 7, Line 27,
 "main duct and the liquid fluid is lead through said main duct" should read
 --main duct and the liquid fluid is led through said main duct--;

Col. 8, Line 3,
 "main brunch 1 may reach the discharging point prior to the" should read
 --main branch 1 may reach the discharging point prior to the--;

Col. 8, Line 60,
 "device of FIG. 7 comprises a main duct 1 splitting of in two" should read
 --device of FIG. 7 comprises a main duct 1 splitting off in two--;

Col. 9, Line 46,
 "ply the data to a control unit at least one led of the sensor 8" should read
 --ply the data to a control unit at least one lead of the sensor 8--;

Col. 9, Line 47,
 "must be lead through the wall of the dead-end channel 3. This" should read
 --must be led through the wall of the dead-end channel 3. This--;

Signed and Sealed this
Nineteenth Day of January, 2016

Michelle K. Lee
*Director of the United States Patent and Trademark Office*

CERTIFICATE OF CORRECTION (continued)
U.S. Pat. No. 8,943,894 B2

Col. 10, Line 8,
"FIG. 11 a shows another embodiment of the device of the" should read
--FIG. 11*a* shows another embodiment of the device of the--; and Col. 10, Line 18,
"LED diode or a laser diode, for example. The angel of light" should read
--LED diode or a laser diode, for example. The angle of light--.